US008225640B2

(12) United States Patent  
Nelson et al.

(10) Patent No.: US 8,225,640 B2
(45) Date of Patent: Jul. 24, 2012

(54) SOOT SENSOR AND METHOD FOR SENSING SOOT

(75) Inventors: Charles Scott Nelson, Fenton, MI (US); Raymond L. Bloink, Swartz Creek, MI (US); Wayne A. Patterson, Attica, MI (US)

(73) Assignee: Delphi Technologies, Inc., Troy, MI (US)

( * ) Notice: Subject to any disclaimer, the term of this patent is extended or adjusted under 35 U.S.C. 154(b) by 736 days.

(21) Appl. No.: 12/332,922

(22) Filed: Dec. 11, 2008

(65) Prior Publication Data

US 2010/0147052 A1 Jun. 17, 2010

(51) Int. Cl.
*G01N 37/00* (2006.01)
(52) U.S. Cl. .................................. 73/28.01
(58) Field of Classification Search ............ 73/28.01, 73/23.2, 61.71, 204, 424, 426, 31.05, 23.31, 73/23.33

See application file for complete search history.

(56) References Cited

U.S. PATENT DOCUMENTS

| 4,300,990 A * | 11/1981 | Maurer ..................... 204/412 |
| 6,300,576 B1 | 10/2001 | Nakamura et al. |
| 6,634,210 B1 * | 10/2003 | Bosch et al. ............... 73/23.33 |
| 2007/0119233 A1 * | 5/2007 | Schnell et al. ............. 73/28.01 |
| 2008/0282769 A1 | 11/2008 | Nelson |
| 2008/0283398 A1 | 11/2008 | Nelson |

FOREIGN PATENT DOCUMENTS

WO   WO 2008117853 A1 * 10/2008

* cited by examiner

*Primary Examiner* — Hezron E Williams
*Assistant Examiner* — Jamar Ray
(74) *Attorney, Agent, or Firm* — Mark H. Svoboda

(57) ABSTRACT

A soot sensor and method for detecting soot is provided. In one exemplary embodiment, a sensing element for a soot sensor is disclosed herein, the sensing element having a pair of peripheral edge sensing electrodes each having a portion disposed on a peripheral edge of a non-conductive substrate of the sensing element; a first pair of side sensing electrodes disposed on a first side of the sensing element, the first side having a first area partially bounded by the peripheral edge, wherein a resistance between the pair of peripheral edge sensing electrodes decreases as soot accumulates on portions of the pair of peripheral edge sensing electrodes and a resistance between the first pair of side sensing electrodes decreases as soot accumulates on portions of the first pair of side sensing electrodes.

4 Claims, 8 Drawing Sheets

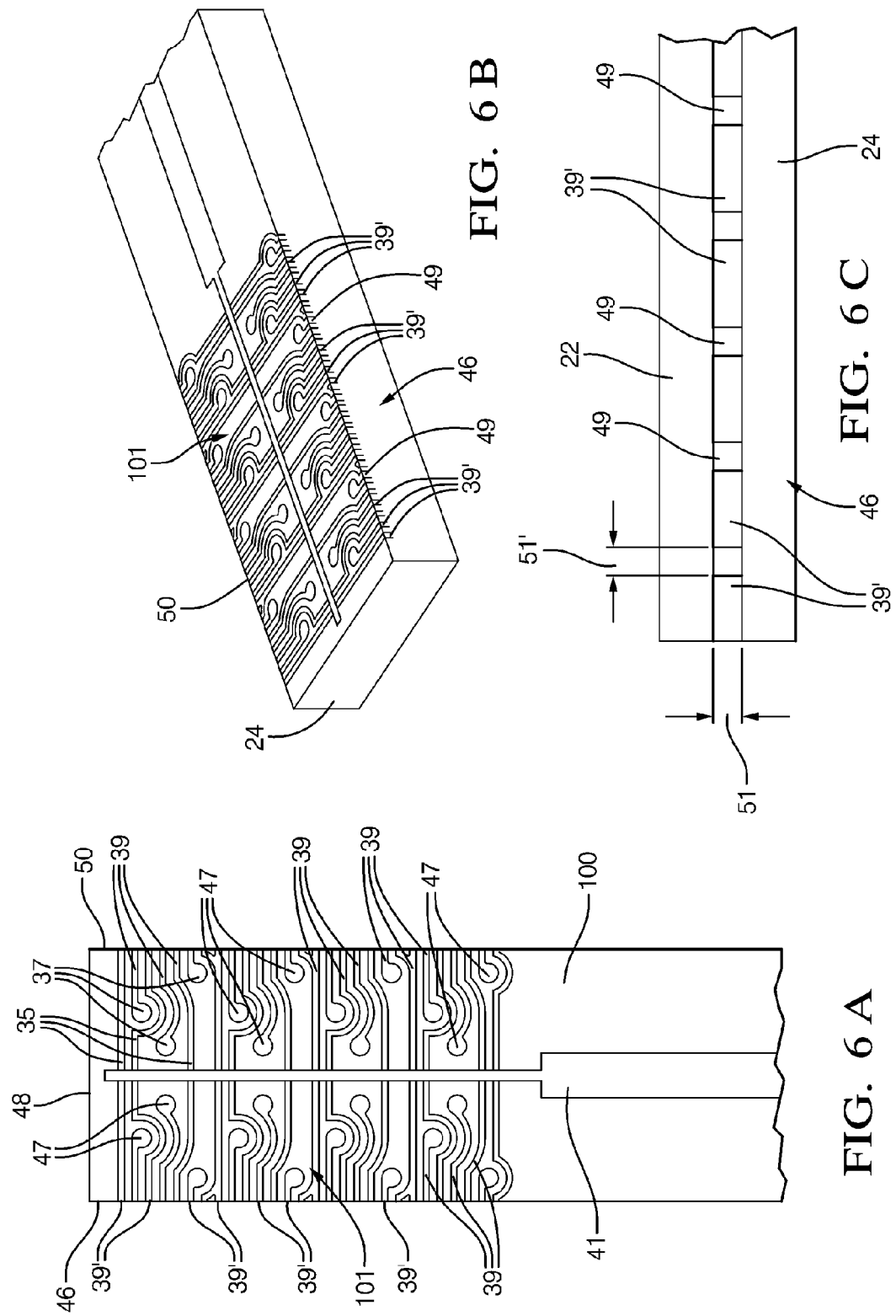

SOOT SENSOR AND METHOD FOR SENSING SOOT

BACKGROUND

Exemplary embodiments of the present invention relate generally to soot sensors and methods for sensing soot.

Soot sensors, used to measure particulate in, e.g., engine exhaust, typically can be established by simple resistive devices. Such a sensor typically consists of a non-conductive substrate, most often alumina, with a screen print pattern using a conductive material, often a precious metal in order to withstand the temperature of a co-fire (although co-fire may not be necessary). In some instances the sensor will also have a heater to heat the soot sensor as required.

The soot sensing portion of the element will have two electrodes with inter-digitized "fingers" that maximizes a perimeter between the two electrodes. When soot from the exhaust lands on the sensor, the carbon makes a high resistance short between the electrodes, effectively lowering the resistance. The more the soot collects, the lower the resistance, and this resistance is measured as an indication of the amount of soot. If it is desired to clean off the soot from the element, the heater on the element is activated to clean off the element. It is also desirable to shorten the distance between the electrodes thus increasing the sensitivity of the signal of the sensing element.

One of the primary issues with soot sensing is that the soot tends to travel by "line of sight", which means that if the soot detecting electrodes are not in the direct line of sight of the soot particles (e.g., rotated by 90 degrees) then the soot will not deposit on the electrodes and generate a signal. Accordingly, there is a need for an orientation insensitive element since it is difficult to orientate the sensor to the exhaust stream. Furthermore and in order to make the soot sensing element more sensitive it is desirable to reduce the spacing between the electrodes and provide more electrode surface area.

Accordingly, is desirable to improve the sensitivity of the soot sensor.

SUMMARY OF THE INVENTION

In one embodiment, a sensing element for a soot sensor is provided, the sensing element comprising: a pair of peripheral edge sensing electrodes each having a portion disposed on a peripheral edge of a non-conductive substrate of the sensing element; a first pair of side sensing electrodes disposed on a first side of the sensing element, the first side having a first area partially bounded by the peripheral edge, wherein a resistance between the pair of peripheral edge sensing electrodes decreases as soot accumulates on portions of the pair of peripheral edge sensing electrodes and a resistance between the first pair of side sensing electrodes decreases as soot accumulates on portions of the first pair of side sensing electrodes.

In another embodiment, a soot sensing system is provided, the soot sensing system comprising: a soot sensor having a sensing element, the sensing element comprising: a pair of peripheral edge sensing electrodes spaced from each other and each having a portion disposed on a peripheral edge of a non-conductive substrate of the sensing element; a first pair of side sensing electrodes spaced from each other and disposed on a first side of the sensing element, the first side having a first area partially bounded by the peripheral edge, wherein a resistance between the pair of peripheral edge sensing electrodes decreases as soot accumulates on portions of the pair of peripheral edge sensing electrodes and a resistance between the first pair of side sensing electrodes decreases as soot accumulates on portions of the first pair of side sensing electrodes, such that an electrical parameter between the pair of peripheral edge sensing electrodes and the first pair of side sensing electrodes is indicative of an amount of soot disposed on the sensing element; and a measuring circuit electrically coupled to the pair of peripheral edge sensing electrodes and the first pair of side sensing electrodes of the soot sensor, the measuring circuit configured to generate a signal indicative of the electrical parameter.

In still another embodiment, a method for measuring an amount of soot accumulated upon a sensing element of a soot sensor is provided, the method comprising: measuring a resistance between a pair of peripheral edge sensing electrodes spaced from each other and each having a portion disposed on a peripheral edge of a non-conductive substrate of the sensing element; measuring a resistance between a first pair of side sensing electrodes spaced from each other and disposed on a first side of the sensing element, the first side having a first area partially bounded by the peripheral edge; determining an amount of soot accumulated on the sensing element by monitoring the resistance between the pair of peripheral edge sensing electrodes and the first pair of side sensing electrodes.

BRIEF DESCRIPTION OF THE DRAWINGS

FIG. 6A is a enlarged partial view of a portion of the sensing element illustrated in FIG. 6;

FIG. 6B is a partial perspective view of the portion of the sensing element illustrated in FIG. 6;

FIG. 6C is a partial side view of portions of the sensing element illustrated in FIGS. 6-6B;

DETAILED DESCRIPTION OF EXEMPLARY EMBODIMENTS

Figure 1:
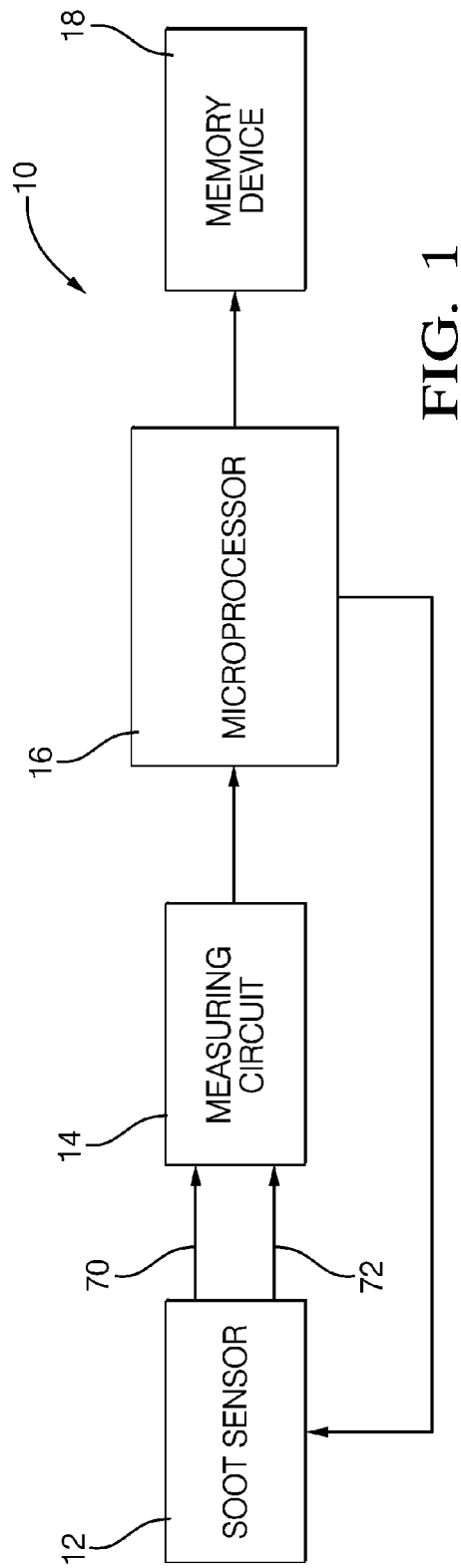
FIG. 1 is a block diagram of a soot sensing system in accordance with various embodiments of the present invention.

Reference is made to the following U.S. Pat. No. 6,634,210 and U.S. Patent Publication Nos., 2008/0283398 A1 and 2008/0282769 A1 the contents each of which are incorporated herein by reference thereto. The present disclosure relates to a particulate or soot sensor wherein the sensing element of the sensor is orientation insensitive or in other words multiple surfaces at different orientations are positioned to come in contact with soot in a gas stream the sensing element is positioned in thus, the sensing element will have surface positioned to be a direct path of the gas flow regardless of the orientation of the sensing element. Furthermore, various embodiments of the present invention are directed to making the element more sensitive by reducing the spacing between the sensing electrodes and providing more electrode surface area.

Various embodiments relate to the construction of an orientation insensitive soot sensor. In general, thick film screen printing is used to print a heater, vias, electrodes, and leads of conductive ink. This invention allows for the construction of the soot sensor to be constructed with HTCC (high temperature ceramic co-fire) tape, or on pre-fired alumina substrate.

In one embodiment a particulate or soot sensing system is provided wherein the system comprises a sensor in electrical communication with a sensor circuit, which operates to detect the level of particulate matter in the environment surrounding the sensor. The particulate sensor system may be calibrated to detect a specific amount of particulate accumulation on the sensor, at which point the particulate sensor system removes the particulates (self-regeneration) by signaling a heater disposed in the sensor. Additionally, a temperature sensor may be advantageously used to maintain the external temperature surrounding the sensor at a point higher than the condensation point of water but lower than the condensation point of the particulates such that the particulates can condense on the sensor without an accompanying condensation of water. Preferably the external temperature maintained by the heater is above the temperature of water condensation, and below the burn-off temperature of the deposited particulates.

The particulate sensor system can self-regenerate by a signal comprising an electrical communication between at least two sensing electrodes and a heater. A signal is transmitted from the sensing electrodes to the heater when the electrical resistance between the sensing electrodes drops to a predetermined threshold amount. Such a drop in resistance is caused by particulate condensation on the sensor. The signal activates the heater to increase its thermal energy output, thereby causing the removal of the particulates from the sensor. As the particulates are removed from the sensor, the resistance gradually increases. The increasing resistance can be employed to signal the heater to decrease its thermal energy output, or the thermal energy output can be maintained until the resistance reaches a selected level, or thermal energy output may be controlled at timed intervals.

In general, the sensor comprises a sensing element and a heating element, wherein the sensing element may comprise, but is not limited to, at least two sensing electrodes, and, wherein the heating element may comprise, but is not limited to, a temperature sensor, and a heater. The sensor may include a multi-layered structure comprising the sensing element, the temperature sensor, the heater, and a combination comprising at least one of the foregoing, contained in a single structure formed, e.g., by multi-layer technology.

The sensing electrodes can include electrically conductive materials or metals, such as, gold, platinum, osmium, rhodium, iridium, ruthenium, aluminum, titanium, zirconium, and the like, as well as, oxides, cermets, alloys, and combinations comprising at least one of the foregoing metals. Each sensing electrode may be composed of the same or different material as the other sensing electrode(s).

The sensing electrodes can be formulated in any fashion. Preferably, however, the sensing electrodes are formed by first preparing an ink paste by mixing an electrode forming-metal powder (e.g., platinum, gold, osmium, rhodium, iridium, ruthenium, aluminum, titanium, zirconium, and the like, or combinations of at least one of the foregoing) with oxides in a sufficient amount of solvent to attain a viscosity suitable for printing. The oxides used to form the sensing electrodes may include those oxides that do not promote the oxidation of particulates and that do not lower the burn-off temperature of the particulates. The ink paste forming the sensing electrode can then be applied to an electrode substrate via sputtering, chemical vapor deposition, screen printing, flame spraying, lamination, stenciling, or the like, with screen printing particularly preferred. In some embodiments, a laser etching method may be performed to provide the necessary gaps between the sensing electrodes wherein the gaps are very small thus increasing the sensitivity of the sensing element. One non-limiting type of sensing electrodes and method for making sensing electrodes is disposed in the following U.S. patent application Ser. No. 11/998,238 filed Nov. 29, 2007, the contents of which are incorporated herein by reference thereto. Other embodiments may use the aforementioned processes to provide the necessary gaps.

Both the heater and the temperature sensor, forming in whole or in part, the heating element, can comprise various materials. Possible materials include platinum, gold, palladium, and the like; and alloys, oxides, and combinations comprising at least one of the foregoing materials, with platinum/alumina, platinum/palladium, platinum, and palladium preferred. The heater and temperature sensor can be applied to the sensor in any fashion, such as by sputtering, chemical vapor deposition, screen printing, flame spraying, lamination, and stenciling among others.

The sensor may further comprise various substrates useful in electrically isolating and protecting the sensing element and the heating element from the temperature surrounding the sensor and/or from the thermal reduction of the condensed particulates during the self-regeneration cycles. The substrates may include, but are not limited to, an electrode protective layer, an electrode substrate, an isolation layer, an insulating temperature substrate, a heater substrate, insulating substrates, wherein the number of insulating substrates is sufficient to prevent disruptive ionic or electrical communication between the heating element and the sensing electrode.

The substrates can comprise non-ionically conducting, electrically insulating materials. Possible electrically insulating materials include oxides, such as alumina, zirconia, yttria, lanthanum oxide, silica, and combinations comprising at least one of the foregoing, or any like material capable of inhibiting electrical communication and providing physical protection, wherein alumina is particularly preferred. Although the composition of the individual substrates can vary, preferably they comprise a material having substantially similar coefficients of thermal expansion, shrinkage characteristics, and chemical compatibility in order to minimize, if not eliminate, delamination and other processing problems.

In general, each of the substrates can be of sufficient size to support the entire length of the sensing electrodes, the temperature sensor, and/or the heater. The thickness of each substrate can be determined based on the desired thermal response time of the self-regeneration cycle, where shorter thermal response times require a smaller thickness. The substrates can be formed using ceramic tape casting methods, and the like.

The sensor may further comprise various leads responsible for electrically communicating the sensor with the sensor circuit. One end of each sensing electrode, one end of the soot sensor and one end of the heater preferably has a connecting point to which one end of at least one lead may be attached.

Preferably, each sensing electrode is electrically connected with at least one lead extending from one end of each sensing electrode to via holes formed on the isolation layer; the soot sensor is electrically connected with at least one lead extending from one end of soot sensor to via holes formed on the insulating substrate; and the heater is electrically connected with at least one lead extending from one end of the heater to via holes formed on the heater substrate. The via holes formed on the above substrates serve to provide a mechanism for electrically connecting the leads to a top contact pad and a bottom contact pad positioned on the exterior of the sensor. The contact pads provide a contact point between the sensor and the sensor circuit. In one embodiment, the via holes are formed at the end portion of the sensor where the opposite end of the sensor is the sensing tip.

The via holes, top contact pad, and bottom contact pad comprise electrically conductive materials. A general method for forming the via-holed substrate is described in U.S. Pat. No. 6,300,576 the contents of which are incorporated herein by reference thereto. For example, each via hole is formed by penetrating the substrate to form a through-hole as the via hole at the position for wiring, filling the through-hole with a conducting paste, and curing the conducting paste while the substrate is shaped and cured under heat in a heating/pressing step. The conducting paste can be prepared as a paste using conducting particles, a thermosetting resin solution, and, if necessary, a solvent. The thermosetting resin can be selected from resins that can be cured simultaneously in the step of heating/pressing the substrate. An epoxy resin, thermosetting polybutadiene resin, phenol resin, or polyimide resin is preferably used.

For the conducting particles, a conducting particle-forming powder of a metal material that is stable and has a low specific resistance and low mutual contact resistance is preferably used. For example, a powder of gold, silver, copper, platinum, palladium, lead, tin, nickel, and combinations comprising at least one of the foregoing is preferably used.

While the electrodes of a soot sensor must be exposed to the exhaust stream in order to work, they must also be protected from being abraded away from the exhaust gas. In addition, it is also desirable for the electrodes to in some instances have as long of a parallel path of the two electrodes as possible thus providing more sensitivity to the sensing electrodes such that once the carbon or soot shorts the path, the more connections that are made, the higher the signal. Further, the shorter the distance between the paths, the higher the sensitivity of the signal. In some embodiments, the sensing electrodes are directly exposed to the soot containing gas.

Figure 2A:
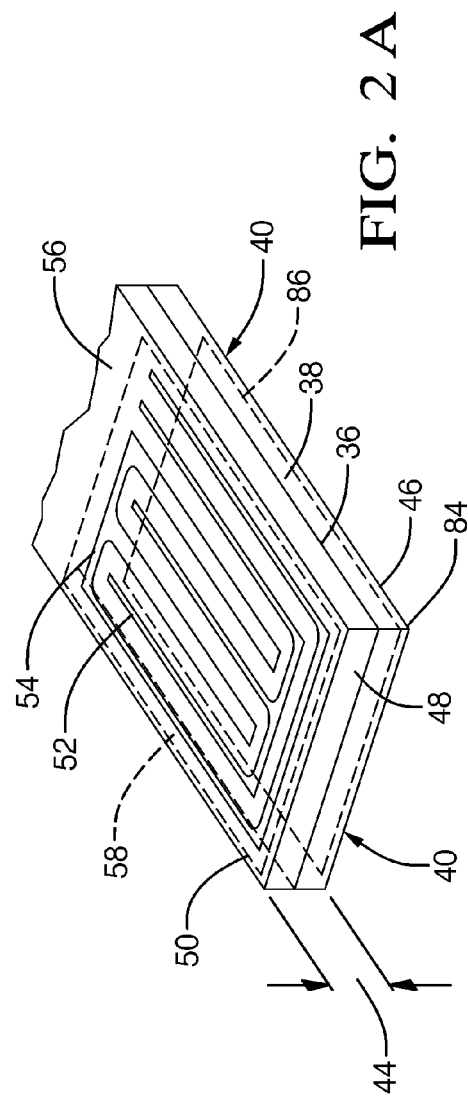
FIG. 2A is a partial perspective view of the sensing element illustrated in FIG. 2.
Figure 2:
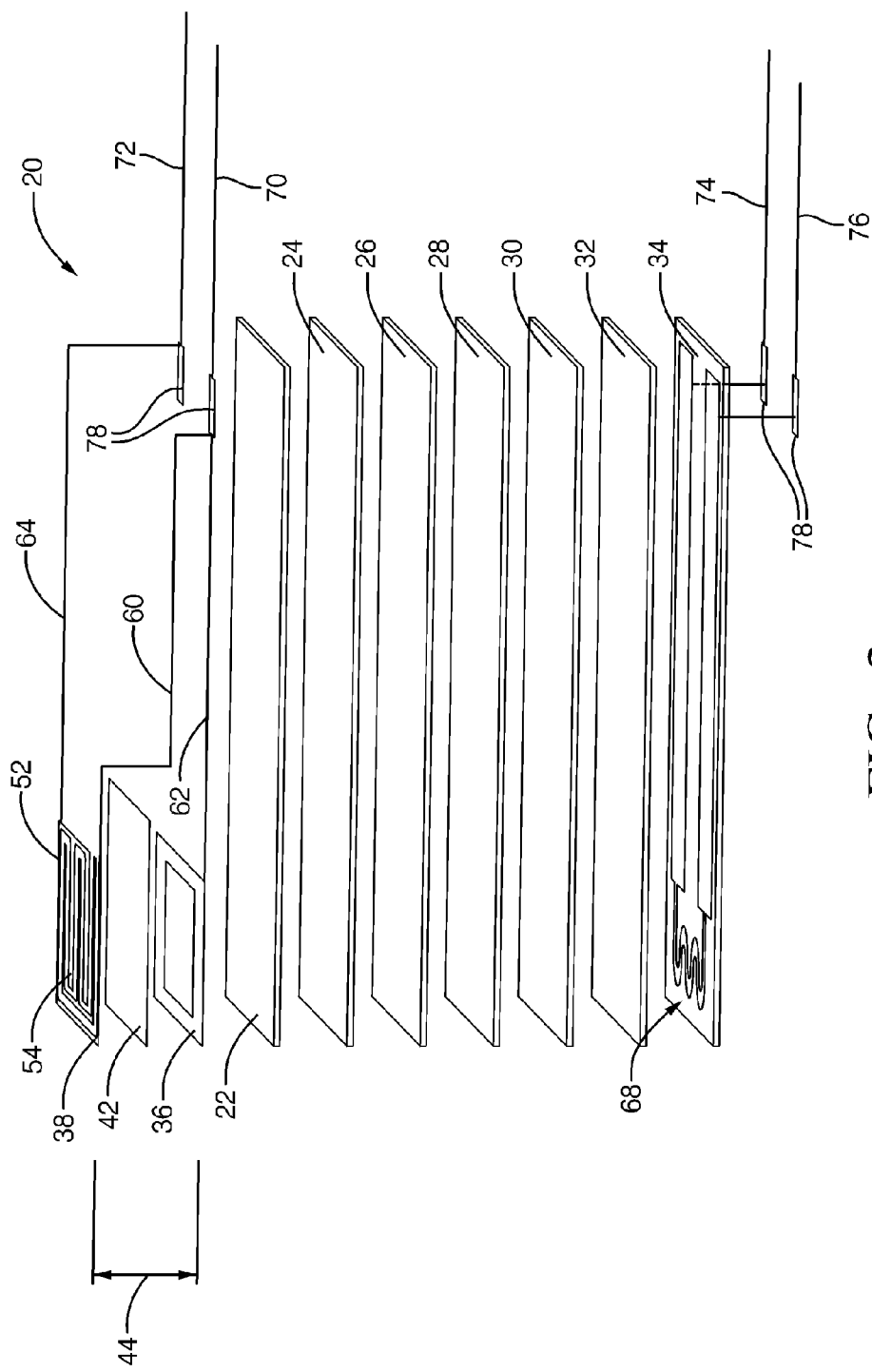
FIG. 2 is an exploded view of a sensing element of a soot sensor in accordance with an exemplary embodiment of the present invention.

Referring to now to FIGS. 1 and 2, a soot sensing system 10 for detecting an amount of soot in an exhaust stream is illustrated. The soot sensing system 10 includes a soot sensor 12, a measuring circuit 14, a microprocessor 16, and a memory device 18.

The soot sensor 12 is provided to detect an amount of soot in an exhaust stream communicating with the soot sensor 12. The soot sensor 12 comprises at least a sensing element 20 with at least two electrodes having portions spaced from each other on a non-conductive substrate such that when soot from the exhaust lands on the sensor and bridges the gap between the electrodes, the carbon of the soot makes a high resistance short between the electrodes, effectively lowering the resistance. The more the soot collects, the lower the resistance, and this resistance is measured by the measuring circuit and signal is provided to the microprocessor as an indication of the amount of soot.

As discussed above, the nonconductive substrate is constructed from an electrically nonconductive material. For example, in one exemplary embodiment the nonconductive substrate is constructed from alumina. Of course in alternative embodiments, the nonconductive substrate could be constructed from other electrically nonconductive materials known to those skilled in the art.

The electrodes are constructed from an electrically conductive material. For example, in one exemplary embodiment, the electrode is constructed from a platinum layer deposited on the non conductive substrate. Of course, in alternative embodiments the electrodes could be constructed from other electrically conductive metallic materials known to those skilled in the art, such as gold, silver, copper, or combinations thereof for example.

It should be noted that an electrical parameter between the electrodes can be utilized to determine an amount of soot that has been deposited on the soot sensor, which is further indicative of an amount of soot in an exhaust stream communicating with the sensor. In one exemplary embodiment, the electrical parameter between the electrodes that is utilized to determine the amount of soot deposited on the sensor is a resistivity level between the electrodes. It should be noted that when soot is deposited between the electrodes a relatively high resistance electrical short is obtained between the electrodes. Thus, as additional soot is deposited on the sensor, a resistivity level between the electrodes is reduced.

Accordingly, the resistivity level between the electrodes can be utilized to calculate the amount of soot that has been deposited on the sensor. Of course, in alternative embodiments other electrical parameters could be utilized to determine the amount of soot deposited on the sensor, such as conductivity level or a capacitance level between the electrodes for example.

The measuring circuit is provided to measure an electrical parameter between the electrodes of the soot sensor that is indicative of an amount of soot deposited on the sensor. In one exemplary embodiment, the electrical parameter is a resistivity level between the electrodes. As shown, the measuring circuit is electrically coupled to the electrodes of the soot sensor, via conductive lines respectively. Further, the measuring circuit is electrically coupled to the microprocessor. During operation, the measuring circuit applies a voltage between the electrodes. In response to the applied voltage, an electrical current flows through the electrodes, the soot deposited between the electrodes to the measuring circuit and the measuring circuit generates a signal indicative of the resistivity level between the electrodes based on an amount of the electrical current. Further, the microprocessor receives the signal from the measuring circuit.

The microprocessor is provided to determine an amount of soot deposited on the soot sensor based on a signal from the measuring circuit. In particular, when the microprocessor receives the signal indicative of a resistance level between the electrodes from the measuring circuit, the microprocessor calculates an amount of soot utilizing an equation such as: amount of soot=f(resistivity level), where f corresponds to an arithmetic function.

Referring now to FIGS. 2 and 2A an exploded view of a sensing element 20 of a soot sensor in accordance with an exemplary embodiment of the present invention is illustrated. As illustrated, the sensing element comprises a multi-layered device having a plurality of electrically insulating layers or substrates 22, 24, 26, 28, 30, 32 and 34 interspersed between the operative electrically conductive elements of the sensor. Of course, the number of layers or substrates and their location may vary.

The sensing element further comprises a pair of peripheral edge sensing electrodes 36, 38 each having a portion disposed on a peripheral edge 40 defined by the non-conductive substrates of the sensing element such that portions of the pair of peripheral edge sensing electrodes are located to detect soot accumulating on the peripheral edge 40 of the sensing element, wherein the peripheral edge of the sensing element may be defined by a plurality of substrates or a plurality of substrates laminated together. As illustrated, the pair of peripheral edge sensing electrodes 36, 38 are electrically isolated from each other by a printed dielectric layer 42. In this embodiment, a gap 44 is disposed between the pair of peripheral edge sensing electrodes 36 and 38 such that soot accumulating on the peripheral edge of the sensing element will bridge gap 44 and create a short between electrodes 36 and 38 (gap 44 is shown in an enlarged view in FIG. 2). Furthermore and as illustrated in FIG. 2A, the electrodes 36 and 38 are provided on three discrete sides 46, 48 and 50 of the sensing element thus providing three sides of sensitivity in three different directions, which in accordance with an exemplary embodiment of the present invention provides an orientation insensitive sensing element.

In addition to electrodes 36 and 38, a first pair of side sensing electrodes 52 and 54 are disposed on a first side 56 of the sensing element wherein the first side has a first area 58 (illustrated by dashed lines) partially bounded by the peripheral edge 40 comprising sides 46, 48 and 50 as well as the contact portions of electrodes 36 and 38 disposed on the peripheral edge. The first pair of side sensing electrodes 52 and 54 are also spaced from each other and positioned to detect soot travelling in directions that may be offset from soot travelling in directions to be detected by the peripheral edge sensing electrodes 36, 38. For example, the first pair of side sensing electrodes 52 and 54 may be positioned to detect soot travelling in directions 90 degrees offset to the detecting surfaces of the peripheral edge sensing electrodes thus, further providing an orientation insensitive sensing element of course, other angular configurations are contemplated. As such, the electrodes 36, 38, 52 and 54 are positioned to be exposed on exterior surfaces of the sensing element so that they can detect soot accumulating on various surfaces of the sensing element.

In this embodiment, electrode 38 of the pair of peripheral edge sensing electrodes is also electrode 52 of the first pair of side sensing electrodes or in other words, the two pairs of sensing electrodes are provided by three electrodes. Accordingly, resistivity is measured between the pair of peripheral edge sensing electrodes via leads 62 and 64, while resistivity between the first pair of side sensing electrodes is measured via leads 60 and 64 (e.g., lead 64 being used twice). The sensing element of FIG. 2 also comprises a heater 68 disposed on layer 34.

The heater is disposed between some of the nonconductive substrates and is provided to maintain the soot sensing element within a desired temperature range. In particular, the heater generates heat in response to a signal received from the microprocessor. In one exemplary embodiment, the heater maintains the nonconductive substrate within a temperature range of 100-500 degrees Celsius when detecting an amount of soot on the soot sensor. The heater can also periodically increase the temperature of the soot sensor to at least 550 degrees Celsius to burn off the collected soot on the soot sensor. Of course, the aforementioned temperatures are merely provided as examples and exemplary embodiments of the present invention are not intended to be limited to the specific temperature ranges provided herein. In one exemplary embodiment, the heater is a metal trace disposed on one of the nonconductive substrates.

In addition, the sensing element may further comprise a temperature sensor (not shown) that is mounted on an insulating temperature substrate to form a temperature sensor element, wherein the temperature sensor element is used to monitor and control the temperature of the heater.

In order to receive the signals from the electrodes and provide control signals to the heater each of the electrodes and the heater are electrically coupled to the microprocessor or other equivalent device via leads 70, 72, 74, 76 that communicate with pads 78 disposed on a surface of the sensing element wherein the pads are in electrical communication with the electrodes and heater and portions of the conductive traces connecting the electrodes and the heater to the pads pass through via holes in the sensing element. It being understood that the lead lines for the heater element do not cross or come in contact with the lead lines for the electrodes for obvious reasons.

As illustrated, the sensing element of FIGS. 2 and 2A provides soot detection on four discrete exterior sides of the sensing element.

Figure 3:
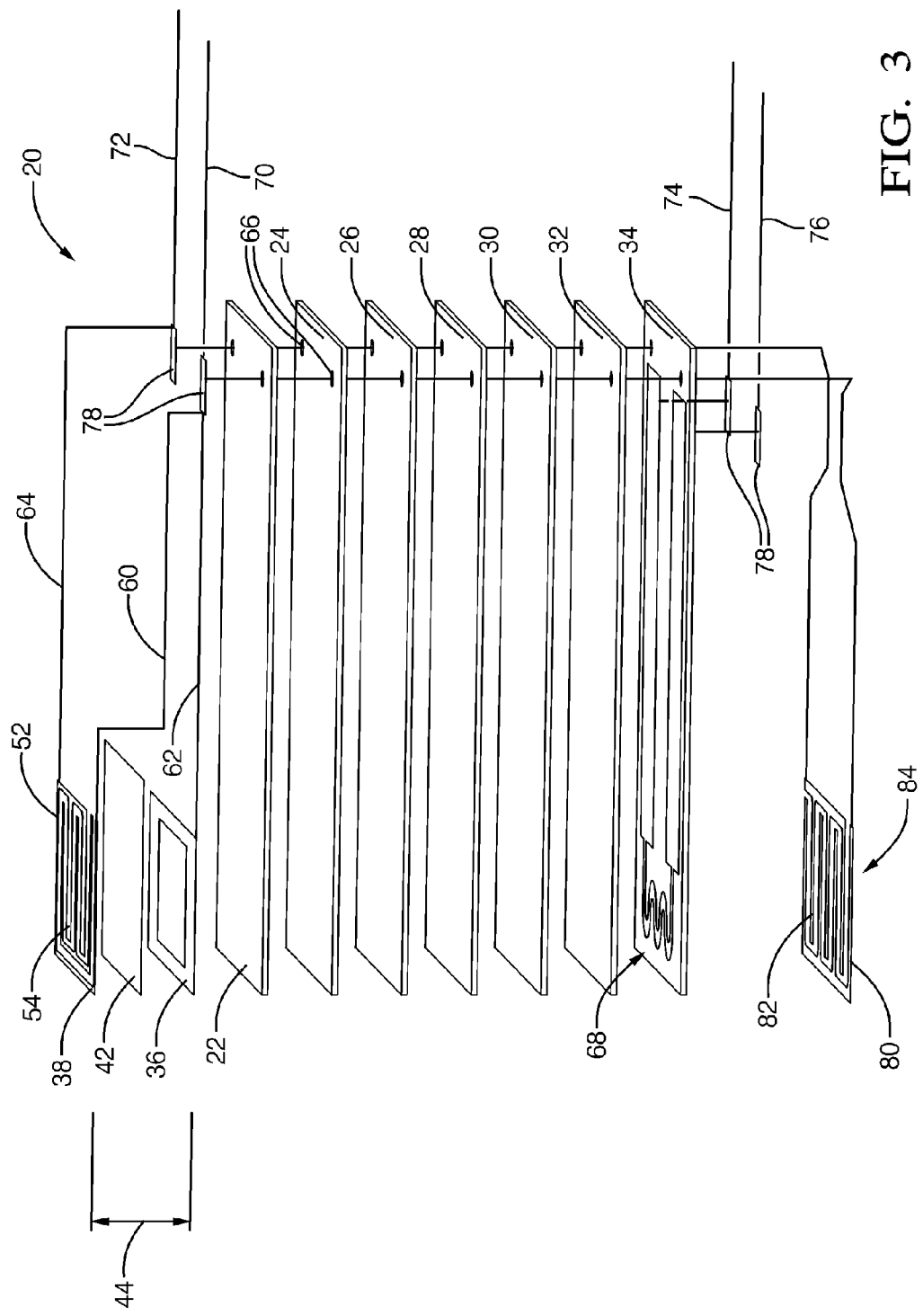
FIG. 3 is an exploded view of a sensing element of a soot sensor in accordance with an alternative exemplary embodiment of the present invention.

Referring now to FIG. 3 another alternative exemplary embodiment of the present invention is illustrated. The FIG. 3 embodiment is similar to the embodiment of FIGS. 2 and 2A however, the sensing element further comprises a second pair of side sensing electrodes 80 and 82 disposed on and spaced apart from each other on a second side 84 (shown in FIG. 2A) of the sensing element wherein the second side is opposite to the first side and has a second area 86 (illustrated by dashed lined in FIG. 2A) and partially bounded by the peripheral edge 40, wherein a resistance between the second pair of side sensing electrodes decreases as soot accumulates on portions of the second pair of side sensing electrodes. In this embodiment, neither one of the pair of peripheral edge sensing electrodes is used in the second pair of side sensing electrodes. Operation of electrodes 80 and 82 is similar to that of electrodes 52 and 54. Moreover and illustrated in the embodiment of FIG. 3, the second side is positioned to detect soot travelling in an opposite direction to soot travelling in a direction that would first contact the first side (See FIG. 2A). Thus, peripheral edge detection and first side and second side detection is provided by five electrodes disposed on an exterior surface of the sensing element. Therefore, the sensing element of FIG. 3 provides soot detection on five discrete sides of the sensing element.

Similar to the previous embodiment, and in order to receive the signals from the electrodes and provide control signals to the heater each of the electrodes and the heater are electrically coupled to the microprocessor or other equivalent device via leads 70, 72, 74, 76 that communicate with pads 78 disposed on a surface of the sensing element wherein the pads are in electrical communication with the electrodes and heater and portions of the conductive traces connecting the electrodes and the heater to the pads pass through via holes 66 in the sensing element. It being understood that the lead lines for the heater element in this and other embodiments do not cross or come in contact with the lead lines for the electrodes for obvious reasons.

Figure 4:
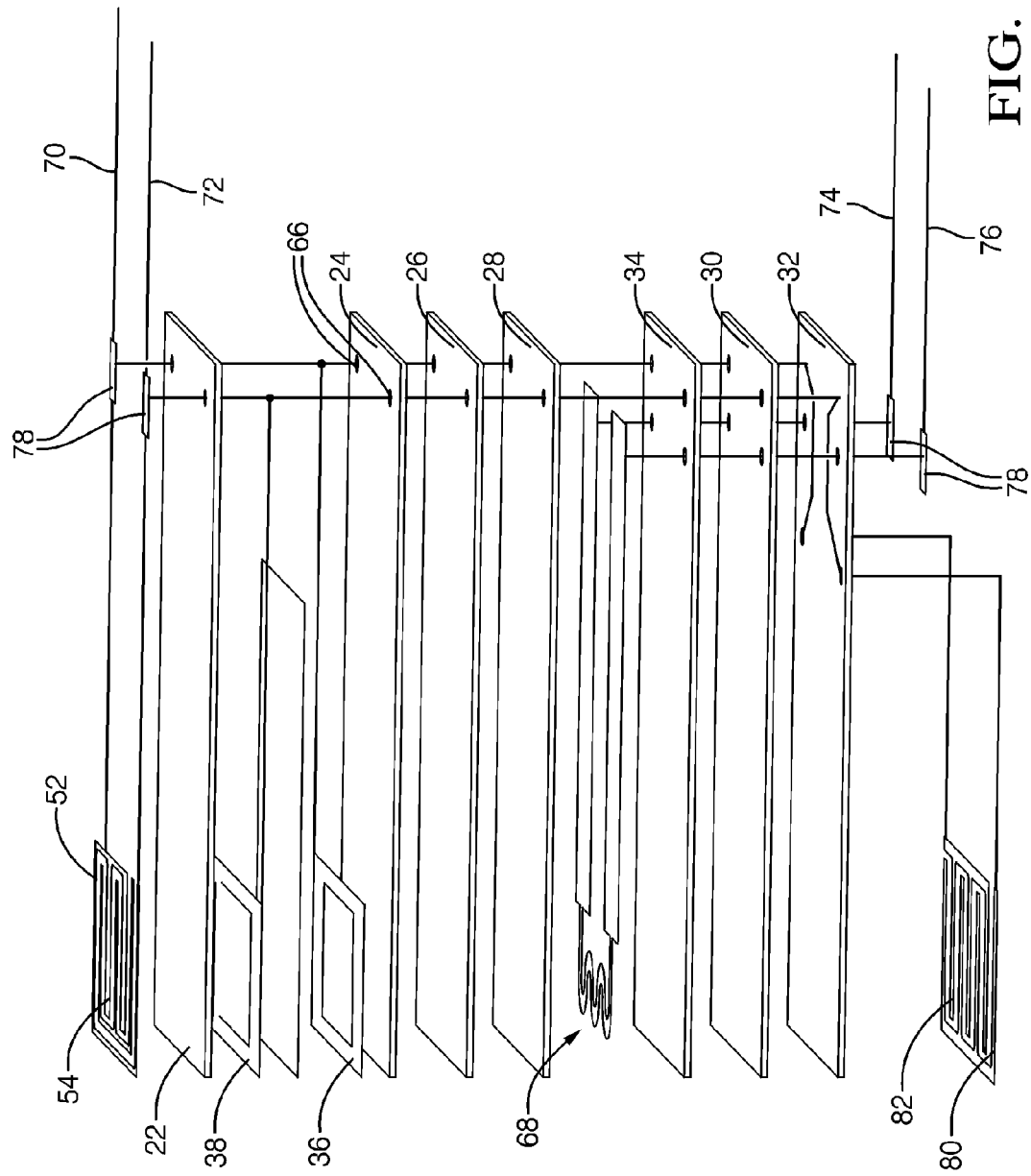
FIG. 4 is an exploded view of a sensing element of a soot sensor in accordance with another alternative exemplary embodiment of the present invention.

Referring now to FIG. 4 another alternative exemplary embodiment of the present invention is illustrated. The FIG. 4 embodiment is similar to the embodiment of FIGS. 2 and 3 however, each of the first pair of side sensing electrodes 52, 54, the second pair of side sensing electrodes 80 and 82 and the pair of peripheral edge sensing electrodes comprise discrete and separate electrodes thus, six electrodes are provided and none of the peripheral edge sensing electrodes are used as either a first side or second side sensing electrode. Similar to the previous embodiment detecting portions of the peripheral edge sensing electrodes are located on the peripheral edge of the sensing element and the first and second side sensing electrodes are positioned in a spaced manner on the first and second sides of the sensing element in areas bounded at least by the peripheral edge. In this embodiment, the printed dielectric 42 is disposed between the pair of peripheral edge sensing electrodes 36 and 38 and the location of the heater is moved. Furthermore, a non-conductive substrate layer is disposed between the pair of peripheral edge sensing electrodes 36 and 38 and the first pair of side sensing electrodes. Therefore, the sensing element of FIG. 4 provides soot detection on five discrete exterior sides of the sensing element.

Similar to the previous embodiments, and in order to receive the signals from the electrodes and provide control signals to the heater each of the electrodes and the heater are electrically coupled to the microprocessor or other equivalent device via leads 70, 72, 74, 76 that communicate with pads 78 disposed on a surface of the sensing element wherein the pads are in electrical communication with the electrodes and heater and portions of the conductive traces connecting the electrodes and the heater to the pads pass through via holes 66 in the sensing element.

Figure 5:
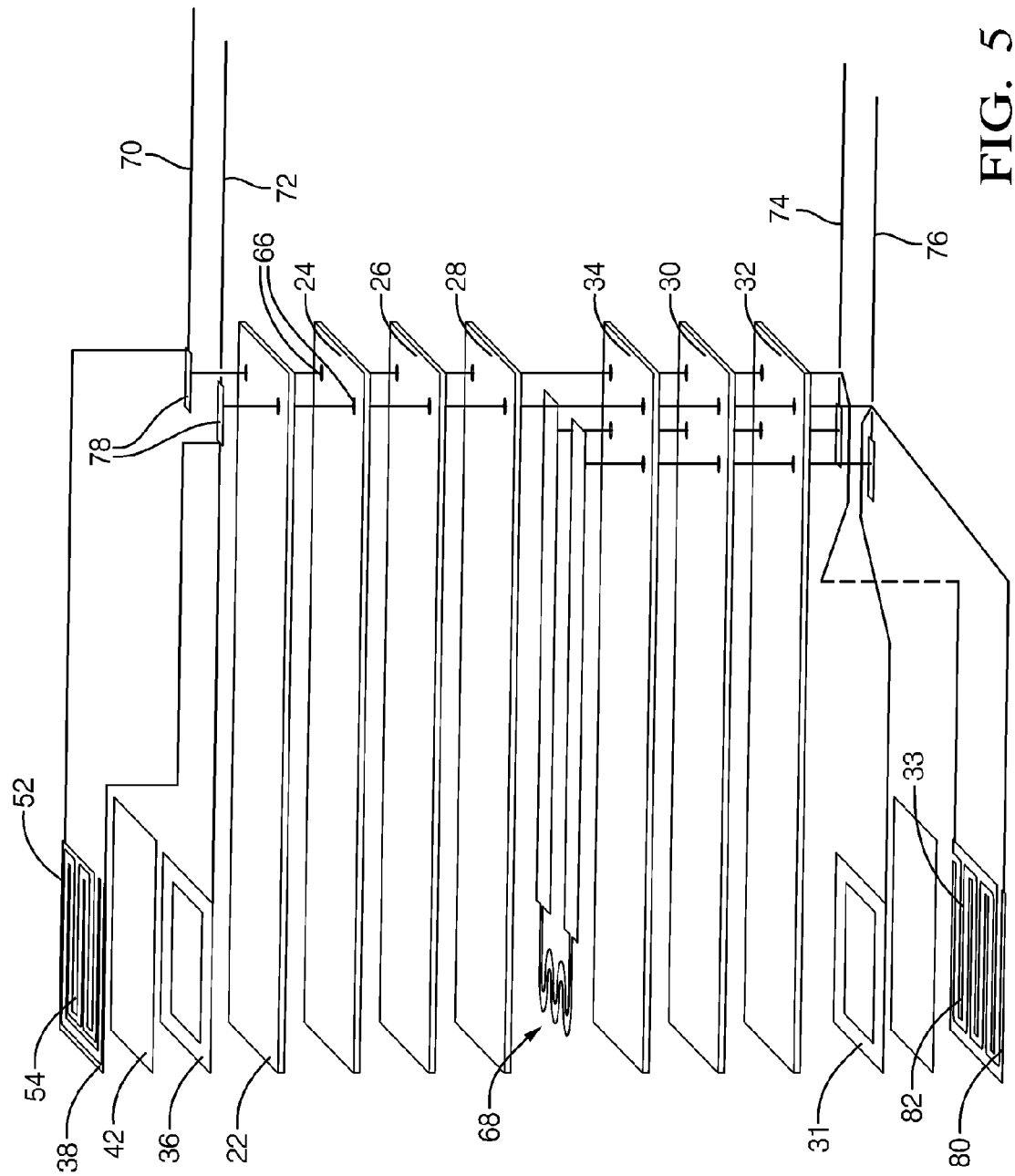
FIG. 5 is an exploded view of a sensing element of a soot sensor in accordance with still another alternative exemplary embodiment of the present invention.

Referring now to FIG. 5 still another alternative exemplary embodiment of the present invention is illustrated. The FIG. 5 embodiment is similar to the embodiment of FIGS. 2-4 however, the pair of peripheral edge sensing electrodes can in one embodiment comprise discrete and separate electrodes separated by a plurality of non-conductive substrates and the heater thus, six electrodes are provided and none of the peripheral edge sensing electrodes are used as either a first side or second side sensing electrode or alternatively two pairs of peripheral edge sensing electrodes are provided 36, 38 and 31, 33 wherein one of the pairs utilizes one of the first side detecting electrodes (38-52) and the other one of the pairs utilizes one of the second side detecting electrodes (33-80) each of which are separated from each other by a printed dielectric thus in this embodiment, eight pairs of sensing electrodes are provided wherein one of the first side and second side sensing electrodes are also used as a peripheral edge sensing electrode.

Once again and similar to the previous embodiments, and in order to receive the signals from the electrodes and provide control signals to the heater each of the electrodes and the heater are electrically coupled to the microprocessor or other equivalent device via leads 70, 72, 74, 76 that communicate with pads 78 disposed on a surface of the sensing element wherein the pads are in electrical communication with the electrodes and portions of the conductive traces connecting the electrodes and the heater to the pads pass through via holes 66 in the sensing element.

Figure 6:
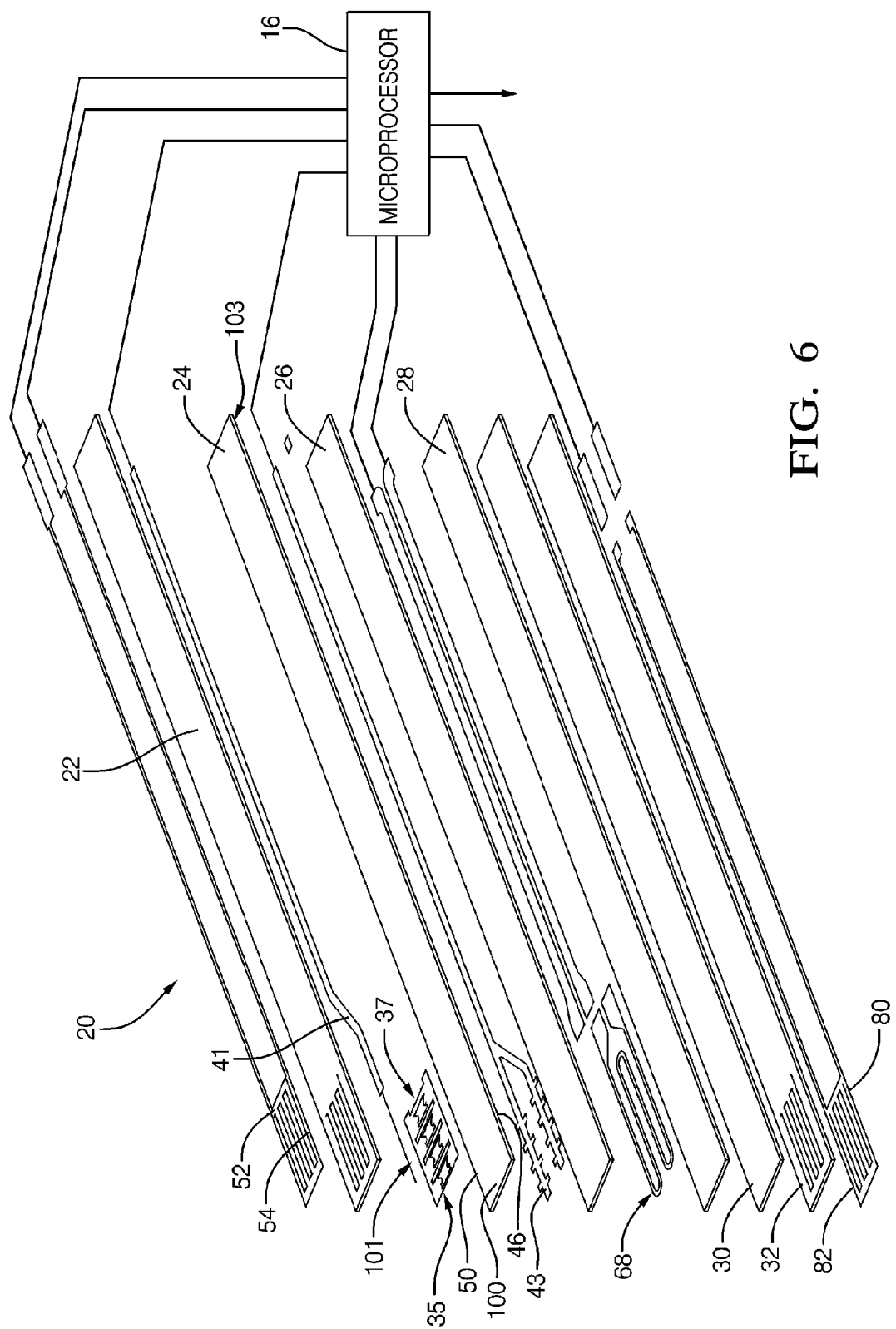
FIG. 6 is an exploded view of a sensing element of a soot sensor in accordance with yet another alternative exemplary embodiment of the present invention.

Referring now to FIG. 6 an exploded view of a sensing element 20 of a soot sensor in accordance with an alternative embodiment of the present invention is illustrated. As illustrated, the sensing element comprises a multi-layered device having a plurality of electrically insulating layers or substrates 22, 24, 26, 28, 30 and 32 interspersed between the operative electrically conductive elements of the sensor. Of course, the number of layers or substrates may vary.

The sensing element further comprises a pair of peripheral edge sensing electrodes 35 and 37 each having a plurality of individual and discrete portions 39 located on a top surface 100 of layer 24 in a spaced manner wherein edge sensing surfaces 39' are located on peripheral edges 46 and 50 of the sensing element and the plurality of individual and discrete portions of each of the peripheral edge sensing electrodes are only located on one of the plurality of non conductive layers and edge sensing surfaces 39' of each of the plurality of individual and discrete portions 39 are located on the peripheral edge of the sensing element and are electrically coupled to either one of a pair of leads 41 and 43 in an alternating fashion, wherein one of the pair of leads is disposed on the top surface 100 of the one of the plurality of non conductive layers and the other one of the pair of leads is disposed on the bottom surface 103 of the one of the plurality of non conductive layers, wherein lead 43 is in electrical communication with every other one of the plurality of individual and discrete portions 39 located on the top surface 100 through via holes 47 in the non-conductive substrate layer. In one embodiment, the via holes are formed in accordance with the processes disclosed in U.S. Pat. No. 6,300,576. Accordingly, the plurality of individual and discrete portions 39 of electrode 37 are in electrical communication with lead 43 by passing through via holes 47. In addition, the plurality of individual and discrete portions 39 of electrode 35 extend from lead 41 across top surface 100 to edges 46 and 50.

FIG. 6A illustrates one non-limiting pattern 101 of plurality of individual and discrete portions 39 of electrodes 35 and 37 disposed on top surface 100 in an alternating and spaced fashion such that soot must bridge a gap between the electrodes to create a short between the electrodes. The pattern is also illustrated in FIGS. 6-6C.

As illustrated in FIGS. 6A and 6B, the plurality of individual and discrete portions 39 located on top surface 100 terminate at the peripheral edge of the non-conductive substrate comprising a portion of the sensing element and the plurality of individual and discrete portions 39 are spaced from each other by a gap 49 that must be bridged by the accumulating soot in order to reduce the resistance therebetween.

In one non limiting embodiment, the gap 49 is provided by laser etching a conductive paste applied to non conductive substrate of the sensing element by for example, the process disclosed in U.S. patent application Ser. No. 11/998,238 the contents of which are incorporated herein by reference thereto of course, the gap may be formed by other processes. As illustrated in FIG. 6B the plurality of individual and discrete portions 39 have an electrode sensing edge 39' exposed at the peripheral edge of the sensing element, which comprises a plurality of non-conductive substrates secured together such that as shown in FIGS. 6A-6C electrode sensing edge or edge sensing surfaces 39' are at a peripheral edge of the substrate and ultimately the sensing element and the individual and discrete portions 39 are disposed between layers 22 and 24. Although FIGS. 6-6C only show one layer comprising individual and discrete portions 39 and edge detecting portions 39'. It is contemplated that multiple layers of separate non-conductive substrates with peripheral edge detection electrodes illustrated in FIGS. 6-6C may be used in exemplary embodiments of the present invention in order to increase the surface area of the peripheral edge sensing electrodes. Or alternatively only a single substrate layer is used for peripheral edge detection. Furthermore and although not shown the individual and discrete portions 39 may be arranged such that edge detecting portions 39' are also located at edge 48 thus providing peripheral edge detection at three sides.

In FIGS. 6A-6C each of the plurality of gaps 49 are partially defined by a dimension 51 of the conductive individual and discrete portions disposed on the non-conductive substrate. Dimension 51 of the individual and discrete portions 39 is vertically illustrated in FIG. 6C and a horizontal or lateral dimension 51' of the gap is also illustrated in FIG. 6C. In one non-limiting exemplary embodiment, the non-conductive substrates and sensing element has a rectangular shape with a length, width and a height and the sensing edge 39' of each of the plurality of individual and discrete portions located on the peripheral edge of the sensing element are parallel to each other and the maximum dimension of each of the plurality of gaps is defined by the height 51 and width 51'. Of course, the plurality of individual and discrete portions located on the peripheral edge of the non-conductive substrate may be orientated in configurations other than those illustrated in the FIGS., e.g., non-parallel, etc.

Accordingly, the embodiment of FIGS. 6-6C illustrates at least a pair of peripheral edge detecting electrodes that are disposed in a single plane (e.g., top surface 100) wherein the electrode sensing surfaces 39' of the individual and discrete portions 39 are located at the peripheral edges of the sensing element to provide the peripheral edge detecting electrodes.

In addition, to the pair of peripheral edge sensing electrodes 35 and 37 the sensing element 20 illustrated in FIG. 6 will also have a first pair of side sensing electrodes 52 and 54, a second pair of side sensing electrodes 80 and 82 and a heater 68. However and in this embodiment, the electrode sensing surfaces 39' of the individual and discrete portions 39 provide the peripheral edge detecting electrodes without one of them being also used in either one of the first or second side sensing electrodes. Similar to the previous embodiments and in order to receive the signals from the electrodes and provide control signals to the heater each of the electrodes and the heater are electrically coupled to the microprocessor or other equivalent device via leads that communicate with pads disposed on a surface of the sensing element wherein the pads are in electrical communication with the electrodes and portions of the conductive traces connecting the electrodes and the heater to the pads pass through via holes in the sensing element.

Moreover and although FIGS. 6-6C only illustrate a four sided soot sensing element, the plurality of individual and discrete portions may also be located on edge 48 to provide a five sided soot sensor.

In one embodiment, the screen printed (or thin film method) pattern is printed on one layer and for the second set of leads and via holes 47 are made through the layer 24 allowing the leads to be joined into a single electrode lead 43 and thus do not cross the first lead 41 disposed on top surface 100.

This pattern could be repeated for several tape layers throughout the sensor, increasing number of pairs of peripheral edge detection electrodes having electrode sensing surfaces 39' at a peripheral edge of the sensing element thus increasing the likelihood of the soot finding a shorting location. For example, numerous non-conductive layers can be configured to have individual and discrete portions 39 with electrode sensing surfaces 39' at a peripheral edge of the non-conductive substrate and the individual and discrete portions 39 and the leads are insulated by the non-conductive layers such that only electrode sensing surfaces 39' are at a peripheral edge of the non-conductive substrate of the sensing element.

FIG. 6B shows that the pattern at the edge is screen printed at the edge with gaps between the electrodes. An improved sensitivity alternative is to purposely short the alternating electrodes at the edge of the layer, and then use a laser to create this separation (e.g., gaps 49). This would be done because there is a limit on how close the alternating patterns can be placed with screen printing. By using a laser to create this separation after screen printing (before the layers are laminated) the alternating electrodes/leads can have a much smaller gap effectively creating greater sensitivity.

In any of the aforementioned embodiments, the first and second side sensing electrodes use a laser or other equivalent processing method to create the gap between the electrodes, and the peripheral edge detection electrodes use either a vertical gap or horizontal gap for soot detection and a laser or other equivalent processing method is used to create the gap (e.g., vertical or horizontal or any other configuration) between the electrodes. Furthermore, there are a variety of connection schemes that could be used to connect the different peripheral edge electrodes with the first and second side electrodes.

Figure 7:
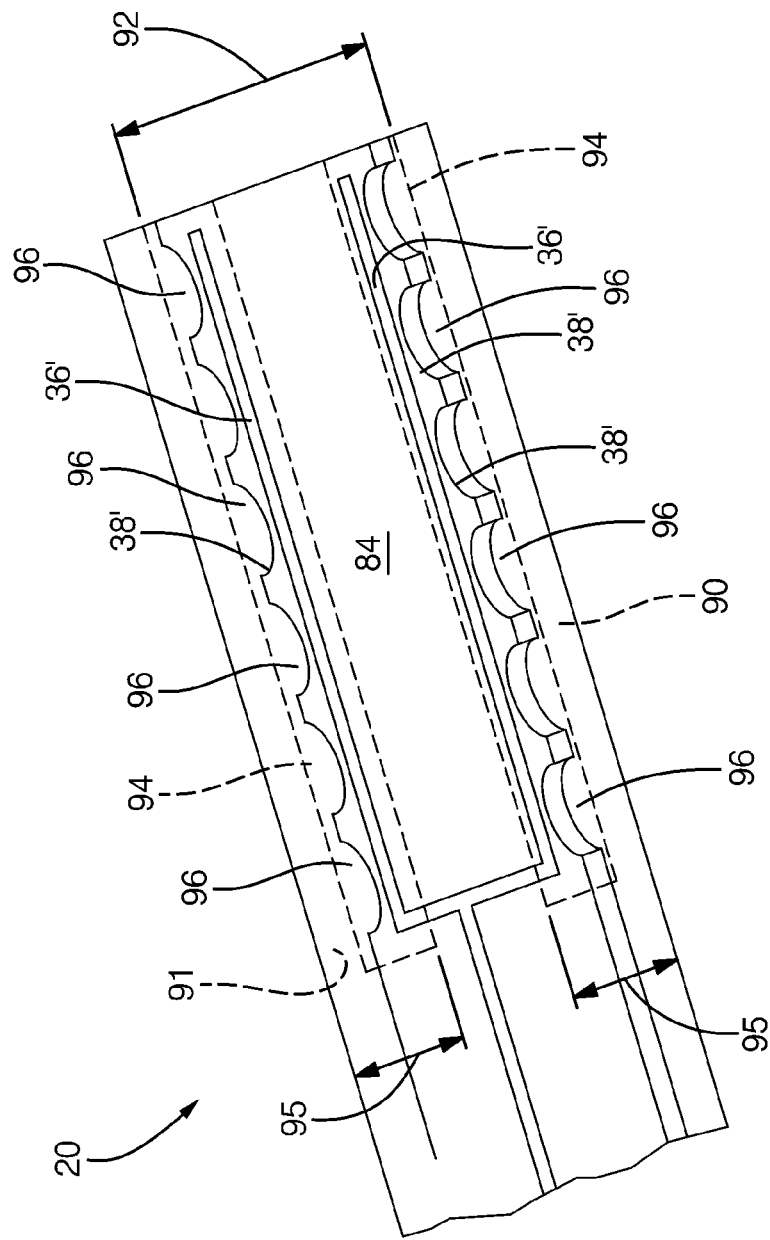
FIG. 7 is a partial perspective view of a sensing element in accordance with yet another alternative exemplary embodiment of the present invention.
Figure 7A:
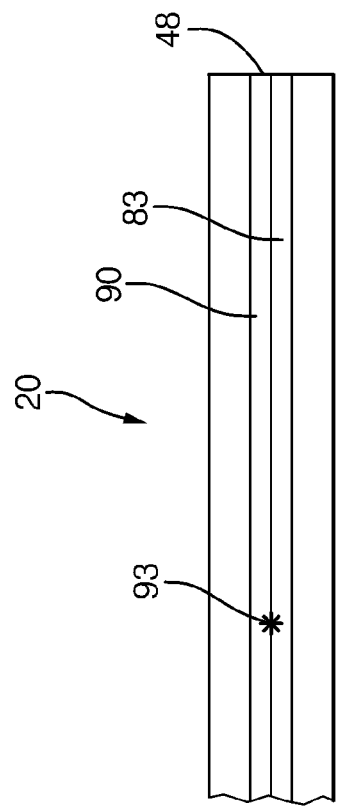
FIG. 7A is partial side view of the sensing element illustrated in FIG. 7 along lines 7A-7A of FIG. 7.

Referring now to FIGS. 7 and 7A still another alternative embodiment of the pair of peripheral edge sensing electrodes is provided. Here the pair of peripheral edge sensing electrodes 36' and 38' are provided on a layer of non-conductive substrate 83. Here portions of each of the sensing portions of the pair of peripheral edge sensing electrodes are disposed on the same surface or plane 84 of the non-conductive substrate. In order to use plane 84 as a peripheral edge sensing electrode portions 94 illustrated by the dashed lines in FIG. 7 are recessed within cavities 90 and 91 and are disposed on either side of the sensing element. In one embodiment, the cavities 90 and 91 are formed by using different sized substrates and laminating them together. Cavities 90 and 91 are configured to have a height 93 and a depth 95 such that peripheral edge sensing electrode portions 94 are capable of being exposed to the soot particles. For example, the height 93 of the cavity will be greater than a corresponding height of the substrate carrying electrodes. Moreover, the width 92 of the non-conductive substrate containing the pair of peripheral edge sensing electrodes is less than the width of the sensing element 20 yet the width 92 of the non-conductive substrate will be large enough so that the electrode are exposed in the cavity when the layers are laminated or secured together. Although the electrodes are illustrated on only two sides of a single substrate, it is also contemplated that the electrodes 36' and 38' may be also positioned on edge 48 of the substrate and multiple substrates and cavities may be provided to increase the amount of peripheral edged detection electrodes. Furthermore and in yet another alternative exemplary embodiment, electrodes may be disposed on both sides of the non-conductive substrate (e.g., top and bottom) and height 93 of cavity is such that when the non-conductive substrate is centrally located in the cavity both the top and bottom sides of the non-conductive substrate are exposed to soot that enters cavity 93.

Accordingly and in this embodiment, the peripheral edge sensing electrode portions can be used with any one of a first and second pair of side sensing electrodes, thus an orientation insensitive sensing element is provided. Furthermore, the peripheral edge sensing electrode portions can be used in any configuration, since the plane or surface 84 is parallel to sides and located in a recess to provide edge detection.

In order to provide the electrodes 36' and 38' on plane 84, a plurality of through holes 96 are located at the edge of the sensor. The through holes are spaced slightly apart. Every other hole is filled from one side of the layer, and the alternating holes are filled from the other side of the layer bottom. When the sensor is singulated along these via hole columns and lines, the only gap keeping the two electrodes from shorting is the space between the holes. As soot fills this gap, the resistance change is detected.

In another method and to provide the electrodes 36' and 38' on plane 84 and as illustrated in FIG. 7, the plurality of through holes 96 are filled along the edge of the sensor, but in this case, all the holes are filled from the same side. On the opposite side of the fill, at a short distance from the holes (the gap) another electrode (e.g., electrode 36' is printed parallel to the row of holes). The gap is filled with an ink that is burned out during the firing process, thus leaving a gap. When soot enters this crevice (made from void left by the burned out ink) and spans the gap between the via holes and the parallel line, a resistance change is detected.

In any of the aforementioned embodiments, the soot sensing electrodes are directly exposed to the gas containing the soot or alternatively if applicable a gas permeable protective layer can be disposed over the electrodes as long as the soot particles can travel therethrough.

While the invention has been described with reference to exemplary embodiments, it will be understood by those skilled in the art that various changes may be made and equivalent elements may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the appended claims. Moreover, the use of the terms first, second, etc. do not denote any order or importance, but rather the terms first, second, etc. are used to distinguish one element from another. Further, the use of the terms a, an, etc. do not denote a limitation of quantity, but rather denote the presence of at least one of the referenced item.

What is claimed is:

1. A sensing element for a soot sensor, comprising:
a pair of peripheral edge sensing electrodes each having a portion disposed on a peripheral edge of a non-conductive substrate of the sensing element;
a first pair of side sensing electrodes disposed on a first side of the sensing element, the first side having a first area partially bounded by the peripheral edge, wherein a resistance between the pair of peripheral edge sensing electrodes decreases as soot accumulates on portions of the pair of peripheral edge sensing electrodes and a resistance between the first pair of side sensing electrodes decreases as soot accumulates on portions of the first pair of side sensing electrodes;
wherein the pair of peripheral edge sensing electrodes are configured to have a plurality of individual and discrete portions each having an electrode sensing edge located on the peripheral edge of the non-conductive substrate of the sensing element and each of the plurality of portions located on the peripheral edge are oriented such that a plurality of gaps are disposed between each adjacent pair of the plurality of individual and discrete portions and its electrode sensing edge located on the peripheral edge, wherein the sensing element comprises a plurality of non conductive layers and the plurality of individual and discrete portions are only located on one of the plurality of non conductive layers of the sensing element.

2. The sensing element as in claim 1, wherein a dimension of each of the plurality of gaps is defined by a dimension of the plurality of individual and discrete portions disposed on the non conductive layer.

3. A sensing element for a soot sensor, comprising:
a pair of peripheral edge sensing electrodes each having a portion disposed on a peripheral edge of a non-conductive substrate of the sensing element;
a first pair of side sensing electrodes disposed on a first side of the sensing element, the first side having a first area partially bounded by the peripheral edge, wherein a resistance between the pair of peripheral edge sensing electrodes decreases as soot accumulates on portions of the pair of peripheral edge sensing electrodes and a resistance between the first pair of side sensing electrodes decreases as soot accumulates on portions of the first pair of side sensing electrodes;
wherein the pair of peripheral edge sensing electrodes are configured to have a plurality of individual and discrete portions each having an electrode sensing edge located on the peripheral edge of the non-conductive substrate of the sensing element and each of the plurality of portions located on the peripheral edge are oriented such that a plurality of gaps are disposed between each adjacent pair of the plurality of individual and discrete portions and its electrode sensing edge located on the peripheral edge,
wherein the sensing element comprises a plurality of non conductive layers and the plurality of individual and discrete portions located on the sensing element are only located on one of the plurality of non conductive layers and each of the plurality of individual and discrete portions are electrically coupled to either one of a pair of leads in an alternating fashion, wherein one of the pair of leads is disposed on one side of the one of the plurality of non conductive layers and the other one of the pair of leads is disposed on the other side of the one of the plurality of non conductive layers.

4. A sensing element for a soot sensor, comprising:
a pair of peripheral edge sensing electrodes each having a portion disposed on a peripheral edge of a non-conductive substrate of the sensing element;
a first pair of side sensing electrodes disposed on a first side of the sensing element, the first side having a first area partially bounded by the peripheral edge, wherein a resistance between the pair of peripheral edge sensing electrodes decreases as soot accumulates on portions of the pair of peripheral edge sensing electrodes and a resistance between the first pair of side sensing electrodes decreases as soot accumulates on portions of the first pair of side sensing electrodes;
wherein the sensing element comprises a plurality of non conductive layers and the pair of peripheral edge sensing electrodes are disposed only on one side of one of the plurality of non conductive layers and each of the pair of peripheral edge sensing electrodes are electrically coupled to one of a pair of leads one of which is disposed on the one side of the only one of the plurality of non conductive layers and the other one of the pair of leads is disposed on another side of the only one of the plurality of non conductive layers.

* * * * *